United States Patent
Lal et al.

(10) Patent No.: US 6,740,058 B2
(45) Date of Patent: May 25, 2004

(54) SURGICAL TOOL WITH INTEGRATED PRESSURE AND FLOW SENSORS

(75) Inventors: Amit Lal, Madison, WI (US); Xi Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 134 days.

(21) Appl. No.: 09/877,714

(22) Filed: Jun. 8, 2001

(65) Prior Publication Data

US 2002/0193817 A1 Dec. 19, 2002

(51) Int. Cl.$^7$ .............................................. A61M 31/00
(52) U.S. Cl. ........................................... 604/65; 604/67
(58) Field of Search ............................... 604/65, 66, 67, 604/93.01, 131–155, 164.11, 246, 247, 264, 272, 30, 31, 118

(56) References Cited

U.S. PATENT DOCUMENTS

| | | |
|---|---|---|
| 4,203,446 A | 5/1980 | Hofert et al. |
| 4,634,420 A | 1/1987 | Spinosa et al. |
| 4,722,348 A * | 2/1988 | Ligtenberg et al. ......... 128/675 |
| 4,924,879 A | 5/1990 | O'Brien |
| 5,158,536 A * | 10/1992 | Sekins et al. ................. 604/20 |
| 5,311,871 A | 5/1994 | Yock |
| 5,318,584 A | 6/1994 | Lange et al. |
| 5,486,162 A | 1/1996 | Brumbach |
| 5,562,610 A | 10/1996 | Brumbach |
| 5,569,968 A | 10/1996 | Lal et al. |
| 5,582,184 A | 12/1996 | Erickson et al. |
| 5,682,233 A | 10/1997 | Brinda |
| 5,728,089 A | 3/1998 | Lal et al. |
| 5,746,217 A | 5/1998 | Erickson et al. |
| 5,820,570 A | 10/1998 | Erickson et al. |
| 5,823,973 A | 10/1998 | Racchini et al. |
| 5,879,310 A | 3/1999 | Sopp et al. |
| 5,879,367 A | 3/1999 | Latterell et al. |
| 6,010,461 A * | 1/2000 | Haniff et al. ................ 600/561 |
| 6,123,718 A * | 9/2000 | Tu et al. ...................... 607/113 |
| 6,443,014 B1 * | 9/2002 | Richter ......................... 73/715 |
| 6,502,983 B2 * | 1/2003 | Yu ................................. 374/44 |
| 6,638,249 B1 | 10/2003 | Lal et al. ..................... 604/151 |

FOREIGN PATENT DOCUMENTS

WO     WO 97/28741     8/1997

OTHER PUBLICATIONS

I.–S. Son, et al., "A Multifunctional Silicon–Based Microscale Surgical System," *Sensors and Actuators*, vol. A 91, pp. 351–356, 2001.

U.S. patent application Ser. No. 09/605,323, Lal et al., filed Jun. 28, 2000.

U.S. patent application Ser. No. 09/617,478, Lal et al., filed Jul. 17, 2000.

Amit Lal, "Micromachined Silicon Ultrasonic Longitudinal Mode Actuators: Theory and Applications to Surgery, Pumping, and Atomization," Ph.D. Dissertation, University of California, Berkeley, 1996, pp. 1–175.

(List continued on next page.)

*Primary Examiner*—Bao-Thuy L. Nguyen
*Assistant Examiner*—Ann Y. Lam
(74) *Attorney, Agent, or Firm*—Foley & Lardner

(57) ABSTRACT

A surgical tool with a rigid body including a needle portion for entering tissue includes a fluid flow channel formed therethrough. A sensor is integrally formed on the tool to detect changing conditions (pressure and/or flow) in the channel. The sensor signal may be used to provide feedback control of pumping of fluid through the channel. The tool may be a micromachined silicon tool with the sensor integrally formed thereon from a silicon nitrate membrane and polysilicon resistors. The tool may be an ultrasonically activated cutting tool, which may be bonded to a package at a node thereof.

12 Claims, 8 Drawing Sheets

OTHER PUBLICATIONS

K. Najafi, et al., "Strength Characterization of Silicon Microprobes in Neurophysiological Tissues," IEEE Transactions on Biomedical Engineering, vol. 37, No. 5, May 1990, pp. 474–481.

D. T. Kewley, et al., "Plasma–Etched Neural Probes," Solid–State Sensor and Actuator Workshop, Hilton Head, South Carolina, Jun. 2–6, 1996, pp. 266–271.

A. Lal, et al., "Silicon Microfabricated Horns for Power Ultrasonics," Transducers '95—Eurosensors IX, Stockholm, Sweden, Jun. 25–29, 1995, pp. 405–408.

A. Lal, et al., "Micromachined Silicon Needle for Ultrasonic Surgery," 1995 IEEE Ultrasonics Symposium, Seattle, Washington, Nov. 7–10, 1995, pp. 1593–1596.

A. Lal, et al., "A Multifunctional Silicon–Based Microscale Surgical System," Hilton Head Conference 2000.

* cited by examiner

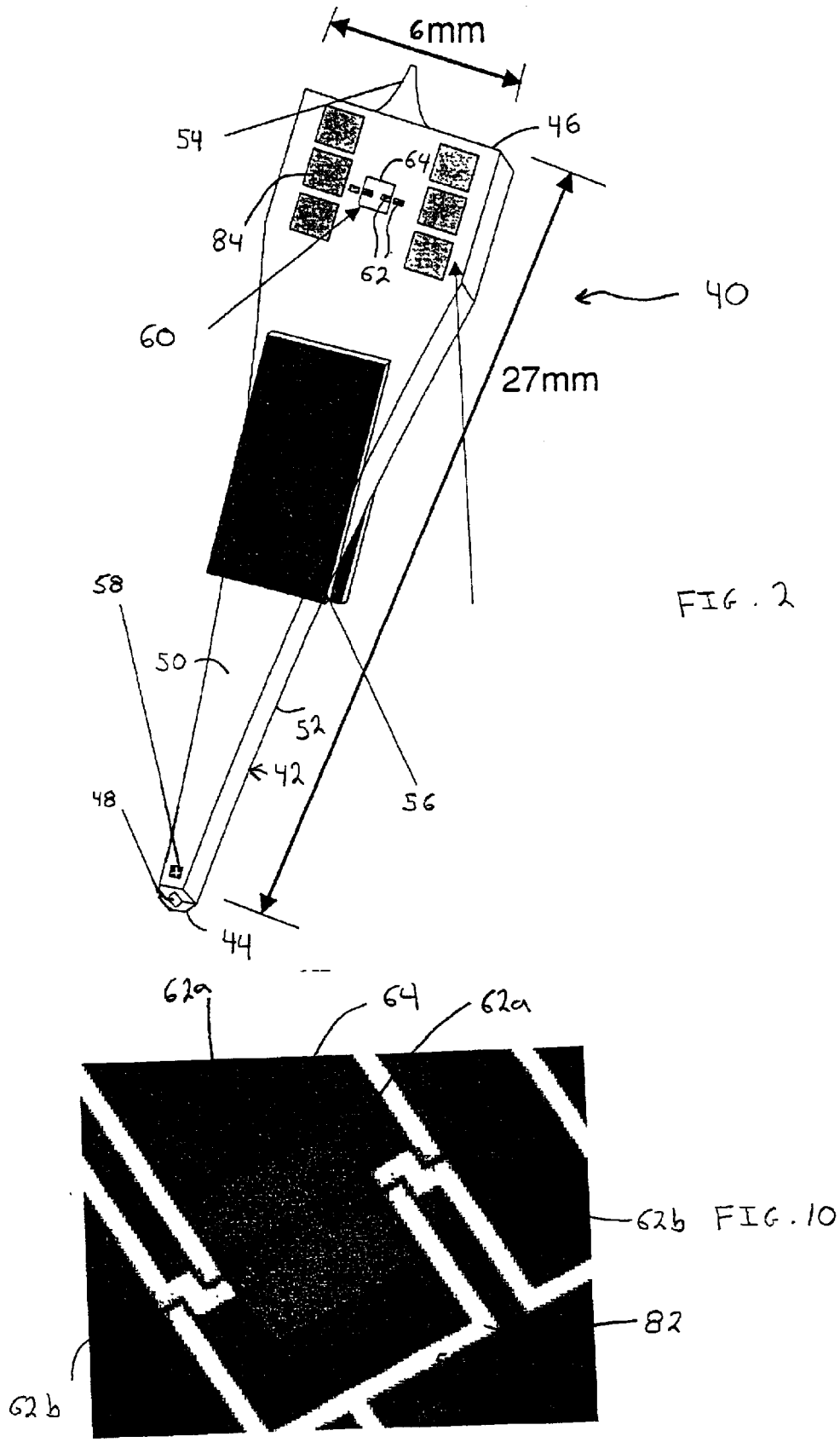

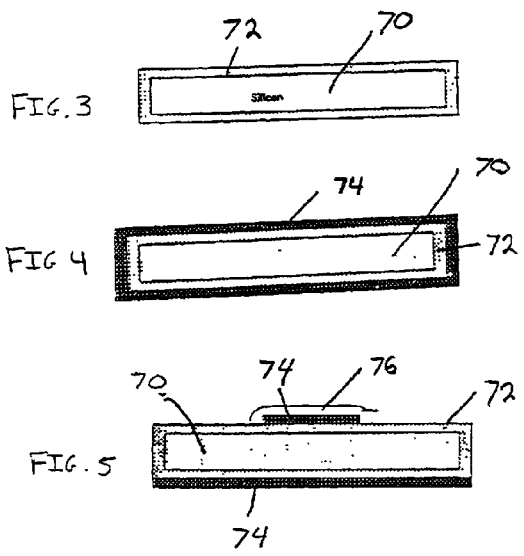
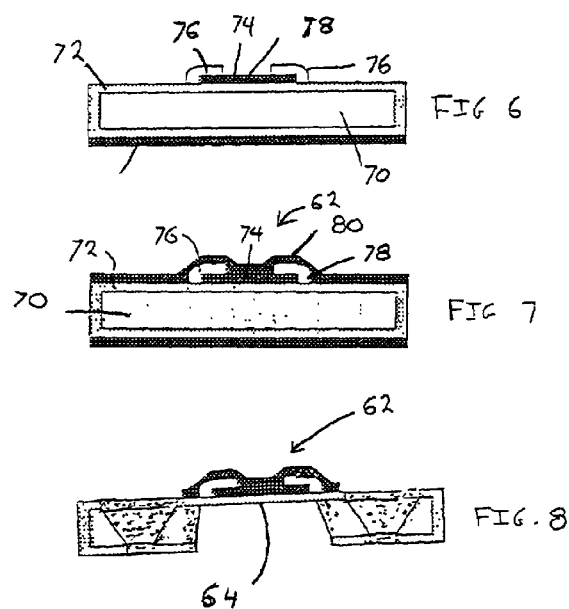
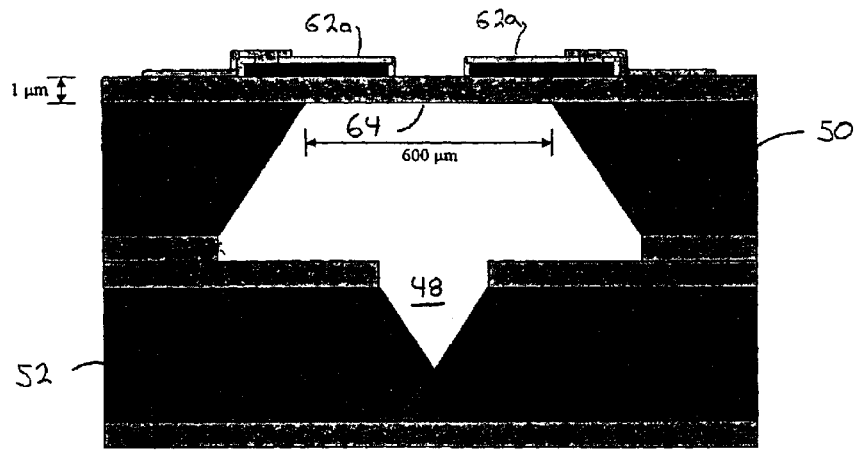
FIG. 9

SURGICAL TOOL WITH INTEGRATED PRESSURE AND FLOW SENSORS

This invention was made with United States government support awarded by the following agency: NSF Grant No: 9985314. The United States has certain rights in this invention.

FIELD OF THE INVENTION

This invention pertains generally to the field of surgical instruments and similar devices, to micromechanical systems, and to ultrasonically actuated instruments.

BACKGROUND OF THE INVENTION

Various medical procedures require the injection of material into and/or the removal of material from a patient. For example, medication or other life sustaining fluids may be required to be injected either intravenously or subcutaneously into a patient. Blood and/or other fluids may be required to be removed from a patient for, e.g., testing, and/or to relieve fluid pressure within the patient's body. Sample cells may be required to be removed from, e.g., a tumor, for testing, preferably without requiring highly invasive surgery. Such medical procedures are typically and preferably performed using a surgical device including a hollow needle, or some similar device, with a rigid needle-like structure for passing into tissue and with a fluid flow channel formed therein. For example, a simple hypodermic needle may be used to inject medication into a patient. A hollow needle positioned in a patient may be connected to a fluid supply, such as a bag of saline solution which may, or may not, include additional medications, and an infusion pump employed to pump fluid from the supply through the needle into the patient. More complicated needle-like surgical instruments may be employed to perform more complicated surgical procedures, such as, for example, removing portions of a tumor or other tissue from a patient's body.

An example of a surgical procedure employing a relatively more complicated needle-like surgical tool is phacoemulsification. Phacoemulsification is the predominant method of removing cataracts (a loss of transparency of the lens of the eye) used throughout the world. Phacoemulsification is a method of emulsifying and aspirating a cataract with a low-frequency ultrasonic needle. An exemplary conventional system 10 for performing phacoemulsification is illustrated in FIG. 1. In such a system 10, a needle-like ultrasonically driven cutting tool 12, with a pointed distal end 14, is provided for cutting and removing a cataract lens. The pointed distal end 14 of the tool 12 penetrates into the eye chamber 16 so as to be positioned in contact with the cataract lens 18 to be cut and removed. The ultrasonic cutting tool 12 is driven longitudinally (e.g., at 40–65 kHz) to fragment the cataracts (deteriorated, cloudy eye lenses) with the hollow vibrating distal tip 14 of the cutter 12. A double lumen channel may be formed running axially from an aperture at the distal tip 14 of the cutter 12 to a proximal end 20 thereof. For example, the double lumen channel may be formed as an outer lumen channel 22 with an inner lumen channel 24 formed running through the length of the outer lumen channel 22. During the process of fragmenting the cataract lens 18, irrigation and aspiration are preferably provided simultaneously through the lumens 22 and 24. For example, irrigation may be provided as a saline solution, provided from a bottle or bag of saline 26, through an, e.g., flexible silicone tube 28, and the outer lumen 22 of the cutting tool 12 to the eye chamber 16. Irrigation maintains the interior chamber pressure as material and fluid are removed from the eye chamber 16. Aspiration may be provided, for example, by a peristaltic pump 30 coupled, e.g., by flexible silicone tubing 32, to the inner lumen 24 at the proximal end 20 of the ultrasonic cutter 12. Operation of the pump 30 is controlled by a control circuit 34. Aspiration serves two purposes. It removes the fragments broken from the cataract lens 18 by longitudinal vibration of the ultrasonic cutter tip 14, and it holds lens particles against the ultrasonic tip 14 to allow efficient fragmentation by pre-stressing the tissue.

Constant pressure monitoring and fluidics control are especially important during aspiration in the phacoemulsification process. If the aperture at the tip 14 of the ultrasonic cutter 12 becomes occluded with tissue fragments, vacuum levels could rise to excessive levels. A sudden release of the occlusion may result in a pressure pulse, which can collapse the anterior chamber 16 of the eye. Thus, it is important to provide feedback to the control circuit 34 of pressure changes in the lumen 24 through which aspiration is performed. In a conventional phacoemulsification system 10, pressure feedback is provided by a pressure sensor 36 located in a control unit, near the control circuit 34 and peristaltic pump 30, but removed from the ultrasonic cutter 12. The pressure sensor 36 is coupled to the ultrasonic cutter 12 via the compliant silicone tubing 32 which couples the pump 30 to the tool. The length of the tubing separating the pressure sensor 36 from the ultrasonic cutter 12 creates a time delay between pressure changes occurring at the tip 14 of the ultrasonic cutter 12 and the detection of such pressure changes by the pressure sensor 36. This time delay, especially resulting from occlusion of the aperture in the cutting tool tip 14, between eye pressure transients and the measured pressure, can cause improper feedback control of the pump, with clinically deleterious effects. In addition to the time delay, the silicone tubing 32 connecting the pressure sensor 36 to the ultrasonic cutter 12 can collapse, causing at least temporary complete loss of pressure feedback. Pressure loss along the tubing 32 can also result in inaccurate pressure feedback measurements. What is desired, therefore, is a reliable system and method for measuring pressure and flow changes in, for example, a needle ultrasonic surgical cutter tool employed as part of a phacoemulsification system, and similar needle-like surgical tools employed for injecting fluids into and removing materials from a patient.

Ultrasonically driven surgical tools, and needle-like surgical tools in general, are conventionally manufactured from appropriate metal materials, such as titanium (for ultrasonic tools) or surgical steel. However, it has been determined that such surgical tools may, advantageously, be implemented as micromachined silicon structures. Such silicon surgical tools may be manufactured to have high strength and sharper cutting tips than similar metal tools, thereby providing for easier cutting. Such tools may be manufactured using conventional low-cost micro-mechanical mass (batch processing) fabrication techniques, which makes such tools low-cost and disposable. Micromachined silicon surgical tools also have the advantage of higher maximum achievable stroke velocity and lower heat generation, due to the high thermal conductivity of silicon, thereby resulting in less tissue damage due to friction induced heating of the tool. Furthermore, sensors and control circuits may be integrated directly onto surgical tools fabricated from silicon using conventional micro-mechanical processing techniques, thereby enabling effective closed circuit control of tool operation. Examples of micromachined silicon ultrasonic needle-like surgical tools include the ultrasonically actuated needle pump system described in U.S. patent application Ser. No. 09/617,478, filed Jul. 17, 2000, by Amit Lal, et al., as well as the vibrationally actuated cutting instrument described in U.S. patent application Ser. No. 09/605,323, filed Jun. 28, 2000, by Amit Lal, et al. The latter describes, for example, a strain sensor integrated onto a silicon vibrationally activated cutting tool to provide an output signal that may be used in a feedback loop to control operation of the tool. For example, a signal provided by the strain sensor mounted near the tip of such a tool may be used as a feedback signal to a feedback controller for controlling an electrical power driver that is connected to supply oscillating power to the tool, so as to maintain the amplitude of the vibrations at a selected level to control, e.g., the cutting and pumping rate of the tool.

SUMMARY OF THE INVENTION

The present invention provides a needle-like surgical tool with an integrated pressure and/or flow sensor thereon. The integrated sensor is coupled directly to a fluid flow channel formed in the surgical tool, through which fluid may be injected into or drawn from a patient using the tool. The sensor is thus able to provide an electrical signal which is immediately responsive to changes in conditions (pressure or flow) in the fluid flow channel. Such electrical signals provided by the sensor may be employed in a feedback loop to control, e.g., a peristaltic pump, or other device, which is coupled to the tool fluid flow channel, thereby to control accurately the pressure and/or flow in the channel. Surgical tools with integrated pressure and/or flow sensors in accordance with the present invention may include, for example, needle-like surgical tools which are employed generically for injecting fluids into or extracting material from a patient, or more sophisticated surgical tools, such as ultrasonically actuated cutting instruments used, for example, in a phacoemulsification system.

A surgical tool with integrated pressure and/or flow sensors in accordance with the present invention may be implemented, for example, as a micromachined silicon device, with integrated pressure and/or flow sensors formed thereon using conventional low-cost mass fabrication processing techniques. For example, a silicon needle with integrated pressure and/or flow sensors in accordance with the present invention may be formed by etching two half needles, with grooves formed along the length of each half needle, out of a silicon wafer using conventional processing techniques. The two half needles are bonded together such that the grooves formed therein form a channel inside the needle through which a fluid may flow. A further etch opening on the backside of one of the half-needles, in fluid communication with the fluid flow channel, results in a thin (silicon nitride) membrane formed as a pressure sensing component in the pathway of the needle channel. Resistors are formed on the membrane (and, preferably, on the rigid surface of the silicon tool nearby), e.g., by depositing a thin polysilicon (LPCVD) film on the membrane, implanting the film with a dopant such as boron, and then patterning the doped polysilicon film into a resistor pattern. Conductors, e.g., aluminum lines, may be formed (e.g., by sputtering) onto the tool, to connect the resistors formed over (and near) the membrane into a circuit configuration (e.g., a Wheatstone bridge circuit), and with connector pads, e.g., also of aluminum, formed on the tool. Wires may be employed to connect the resistor circuit via the connector pads to a supply/amplifier circuit, e.g., provided on packaging to which the tool is bonded.

Load pressure in the surgical tool fluid/flow channel generates stress in the membrane with the resistors formed thereon. This stress results in a change in resistance of the resistors formed over the membrane. Changes in the resistance of the resistors formed over the membrane may be detected essentially instantaneously in response to changes in pressure in the surgical tool fluid flow channel. Thus, the pressure sensor formed by the resistors formed on the membrane may be used to generate a highly responsive feedback signal which may, in turn, be used to control a peristaltic pump, or other device, to control the pressure in the surgical tool fluid flow channel and, therefore, in the area adjacent to the channel aperture formed at the distal end of the tool. Thus, for example, where the present invention is employed with an ultrasonically actuated cutting tool employed for phacoemulsification, the feedback signal provided by a pressure sensor integrally formed on the tool may be employed to provide proper feedback control in response, for example, to occlusion of the cutting needle tip, thereby to prevent damage to the eye chamber in the event of such an occurrence during aspiration of the fragments of an emulsified cataract lens.

A sensor integrally formed on a silicon surgical tool in accordance with the present invention may also be employed to detect other related conditions in the fluid flow channel of the tool. For example, the sensor can also be used to sense fluid flow. Fluid flow in the fluid flow channel modifies the heat transfer from the resistors formed on the membrane. The resistance change due to flow can be sensed and used as a feedback signal. Under free flow conditions the output signal produced by the integral sensor can result from both flow and pressure effects. Thus, both flow and pressure signals can be obtained from such a sensor.

As mentioned above, the present invention may be employed in a micromachined silicon surgical cutting tool for phacoemulsification. Such a tool will have ultrasonic activators bonded thereto for ultrasonically driving the tool. The tool may be formed in a horn shape (e.g., a catenary horn) for focusing ultrasonic energy at the cutting tip of the tool. A pressure/flow sensor in accordance with the present invention is preferably integrally formed near the end of the tool opposite the cutting tip, to minimize the stress concentration factor thereon. A strain sensor may be formed near the tip of the tool, to provide a signal for feedback control of tool oscillation. The entire micromachined silicon cutting tool in accordance with the present invention may be bonded to packaging (such as an IC DIP package), preferable at a null point or displacement node of the horn/needle structure, to minimize coupling of ultrasonic vibration of the tool to the packaging and any circuitry formed thereon.

Further objects, features, and advantages of the present invention will be apparent from the following detailed description taken in conjunction with the accompanying drawings.

BRIEF DESCRIPTION OF THE DRAWINGS

FIG. 2 is a perspective view illustration of an exemplary micromachined ultrasonic silicon surgical tool with an integrated pressure/flow sensor formed thereon in accordance with the present invention.

FIGS. 3–8 are simplified cross-sectional views showing steps in the formation of a half section of a silicon surgical tool with an integrated pressure/flow sensor formed thereon in accordance with the present invention.

FIG. 9 is a simplified cross-sectioned view of a portion of a silicon surgical tool in accordance with the present invention, showing resistors formed on a membrane in communication with a fluid flow channel of the tool to form an integrated pressure/flow sensor thereon.

FIG. 10 is a detailed plan view of polysilicon piezoresistors and a silicon nitride membrane formed on the surface of a silicon surgical tool in accordance with the present invention to form an integrated pressure/flow sensor thereon.

DETAILED DESCRIPTION OF THE PREFERRED EMBODIMENTS

Figure 1:
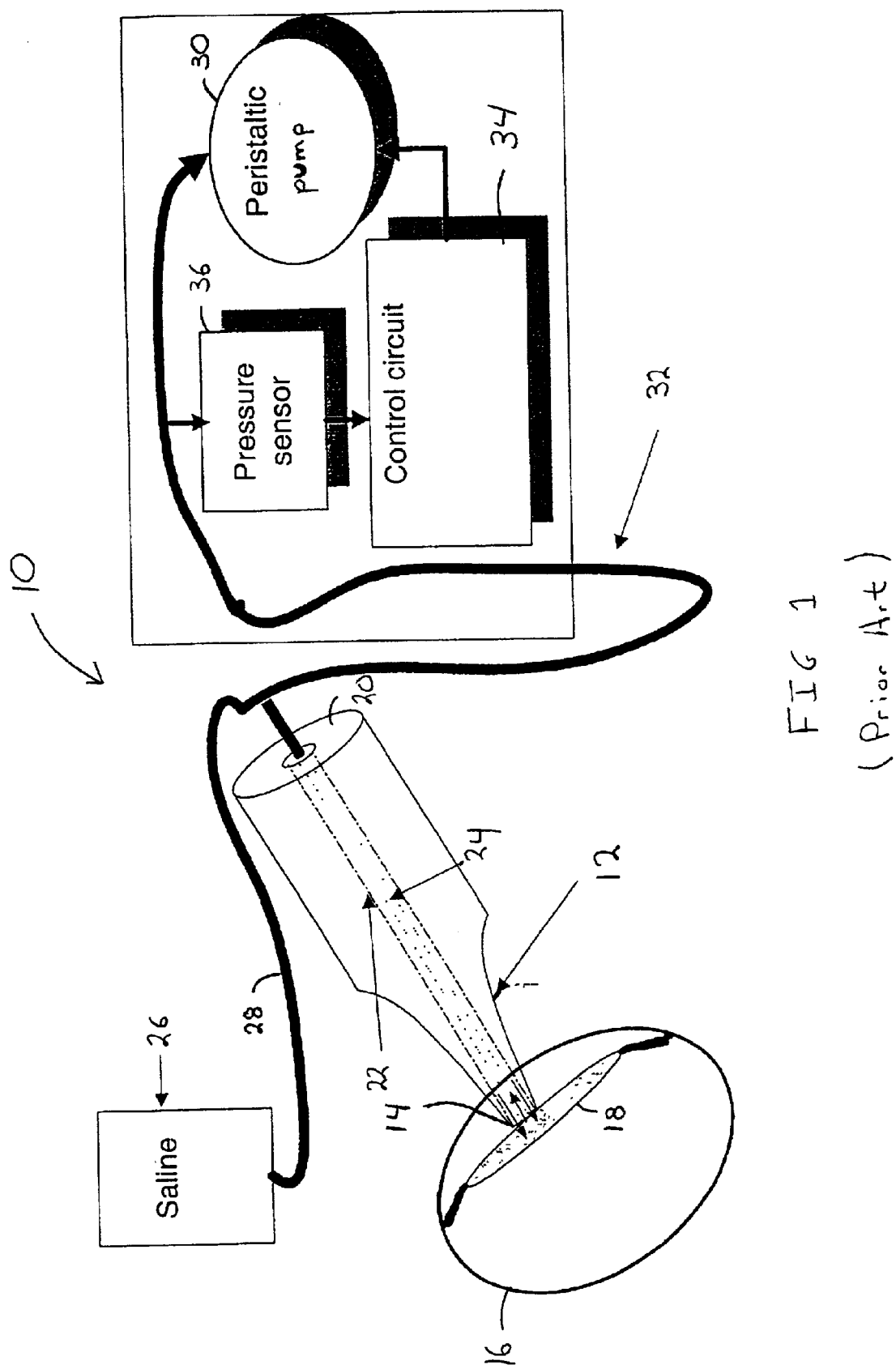
FIG. 1 is a schematic illustration of a conventional phacoemulsification system as known in the art.

The present invention provides a surgical tool with a fluid flow channel formed therein and with a sensor integrally mounted on the tool itself to detect rapid changes in conditions within (e.g., pressure in and/or fluid flow through) the fluid flow channel of the tool. Since the sensor is mounted directly on the tool, a sensor signal provided by the sensor is immediately and accurately responsive to changes in pressure and flow through the tool. This allows for much more effective feedback control of, for example, the pumping of fluid through the fluid flow channel in the tool.

The present invention will be described in detail herein with reference to the exemplary application thereof to a micromachined silicon surgical cutting tool 40, as illustrated in FIG. 2, for use, for example, in a phacoemulsification procedure for removal of a cataract lens. It should be understood, however, that the present invention may be employed in combination with any needle-like surgical tool, or process employing such a tool, where it is desired to monitor accurately the pressure in and/or fluid flow through a fluid flow channel formed in the tool. Such a tool may be micromachined from silicon, as described in more detail herein, or made from any other material using conventional manufacturing processes. Furthermore, it should be understood that a tool, made of silicon or otherwise, with a fluid flow channel formed therein and an integrated pressure and/or flow sensor formed thereon in accordance with the present invention, may be employed in consumer and/or industrial processes other than surgery on humans and/or animals. The present invention may thus be applicable to a variety of processes which may be improved by accurate monitoring and/or feedback of pressure in and/or fluid flow through a fluid channel formed in a needle-like tool for injecting and/or extracting fluid of any type.

An exemplary micromachined silicon surgical tool 40 in accordance with the present invention includes a generally elongated body 42. The body 42 of the tool 40 is preferably generally horn shaped, with the distal end 44 of the horn forming a needle and being more narrow than the proximal end 46 thereof. For example, the tool body 42 may be formed as a catenary horn (i.e., sides curved defined by the cosh function), 27 mm long, and with a shank-to-tip area ratio of 6:1. Of course, a silicon surgical tool in accordance with the present invention may be made in various different dimensions from those indicated. The distal end 44 of the tool 40 forms a cutting end surrounding a central bore or flow channel 48 that extends through the tool from the distal 44 to the proximal 46 end thereof. The silicon based body 42 of the tool may be formed utilizing micromechanical processing techniques conventionally used with silicon in semiconductor manufacturing to provide a cutting tool 40 having relatively small dimensions and high performance. For example, the horn shaped body 42 may be formed of two plates 50 and 52, each formed separately out of a silicon wafer (e.g., 400 $\mu$m thick) by conventional micromechanical processing techniques. Each of the plates 50 and 52 has matching grooves (e.g., 250 micrometers wide) formed on the backside thereof. The matching grooves form the flow channel 48 when the two half-needles are bonded together, using an adhesive, to form the body 42 of the tool 40. A grommet 54, e.g., made of copper, or some other material, is preferably also bonded to the silicon body 42 of the tool 40, at the proximal end 46 thereof, in fluid communication with the flow channel 48, to provide a connection for tubing to the flow channel 48.

At least one, and preferably two, piezoelectric actuators 56 are fixed to the body 42 of the tool 40. The actuators 56 may be implemented, for example, as PZT-4 (lead-zirconate-titanate) ceramic plates (e.g., 0.4 mm×5 mm×10 mm) which are adhesively bonded to the silicon body 42 of the tool 40. The actuators 56 may be driven in a conventional manner by an electrical signal provided thereto to ultrasonically drive (i.e., vibrate) the distal end 44 of the tool 40, thereby allowing the distal end 44 of the tool 40 to cut through tissue and/or other material. The horn shape of the body 42 of the tool focuses ultrasonic energy provided by the actuators 56 through the body 42. Two PZT plates bonded to and driven symmetrically on both sides of the needle minimize the coupling to transverse mode. For the exemplary tool 40 described herein, the needle resonates at its half-wavelength longitudinal node (~173.5 kHz), with a quality factor of 75, and the tip displacement was measured optically to be 5.6 $\mu$m peak-to-peak when driven at 31.6 Vpp. This displacement translates into a tip velocity of ~5.3 m/s and a displacement amplification of 3.5. For the exemplary embodiment described herein, the displacement node is 11.3 mm away from the shank end of the tool.

A piezo-resistive strain sensor 58 may preferably be formed on the surface of at least one of the plates 50, 52 forming the body 42 of the tool 40. Preferably, at least one such strain sensor 58 is formed near the distal end 44 of the tool 40. The strain sensor 58 may be formed as a polysilicon piezoresistor circuit integrally formed on the surface of the tool 40. The strain sensor circuit allows measurement of the magnitude of vibrations of the needle end of the tool 40. By utilizing such a strain sensor 58 or sensors in a feedback control circuit for the driver circuitry used to drive the actuators 56, the amplitude of the vibrations of the tool 40 may be controlled and maintained at selected levels. An exemplary vibrationally actuated cutting instrument with strain sensors integrally formed thereon for this purpose is described in more detail in U.S. patent application Ser. No. 09/605,323, filed Jun. 28, 2000, by Amit Lal and Il-Seok Son, the disclosure of which is incorporated herein by reference.

In accordance with the present invention, a micromachined silicon surgical tool 40 includes a sensor 60 integrally formed thereon to measure a changing condition of (e.g., the pressure in and/or fluid flow through) the fluid flow channel 48 formed in the tool 40. At half-wavelength mode, the two ends of the ultrasonic tool 40 are stress nodes where displacement is maximum and stress is minimum. Thus, the sensor 60 is preferably placed near the rear end of the tool 40 to minimize the stress concentration factor thereon. The sensor 60 is preferably formed as a circuit of polysilicon resistors 62 formed on and near a thin membrane 64 formed in the body 42 of the tool 40. One side of the membrane 64 is in fluid communication with the fluid flow channel 48 through the tool 40. Pressure changes in the fluid flow channel 48 distort the membrane 64 slightly. This distortion is reflected in a change of the resistivity of the polysilicon resistors 62 formed on the membrane 64. Similarly, a flow of fluid through the fluid flow channel 48 will affect a change in temperature and, therefore, a change in resistance, of the polysilicon resistors 62 formed on the membrane 64. The change in resistivity of the polysilicon resistor circuit 62 can be detected as an electrical signal which is, therefore, related to the pressure in and/or flow through the fluid flow channel 48. This electrical signal, which is immediately and accurately responsive to changes in pressure and/or flow in the fluid flow channel 48, may be provided as a feedback signal to a control system for controlling the pumping of fluid through the fluid flow channel 48. As discussed above, a rapid and accurate response to changes in pressure and/or flow through the fluid flow channel 48 can be a critical necessity in surgical procedures employing an ultrasonic cutting tool 40, such as, for example, phacoemulsification.

An exemplary method for integrally forming a pressure/flow sensor circuit 60 on a micromachined silicon tool with a flow channel 48 formed therethrough will now be described in detail with reference to FIGS. 3–9. Of course, it should be understood that other similar or different manufacturing techniques may also be employed to form a pressure and/or flow sensor on a needle-like surgical instrument with a flow channel formed therethrough. For example, it may be preferable first to form the body of a silicon tool from a silicon wafer, to define the fluid flow channel and sensor membrane, followed by the processing described below to form a polysilicon resistor circuit on and near the membrane.

A silicon wafer 70, from which the half parts 50, 52 of the body 42 of the tool 40 will be formed, is coated with low-stress silicon nitride 72. (FIG. 3.) As will be discussed in more detail below, the thickness of the silicon nitride layer 72 may be selected to result in a membrane 64 for the pressure/flow sensor 60 which provides maximum sensitivity while being able to sustain a sufficient pressure load for the desired application. In general, a thickness for the silicon nitride layer 72 of between approximately 1 $\mu$m and 2 $\mu$m may be appropriate. LPCVD polysilicon thin film 74 (e.g., 1.5 $\mu$m thick) is deposited on the silicon nitride 72. (FIG. 4.) The polysilicon piezoresistors 62 forming the sensor circuit will be formed from the polysilicon layer 74. The polysilicon 74 is doped heavily p-type, e.g., by boron implantation at 60 KeV at a dose of $5 \times 10^{15}$/cm$^2$. The polysilicon layer 74 is then annealed, e.g., at 900° C. for 30 minutes, which gives a longitudinal gauge factor of about 20–30. After patterning the polysilicon layer 74 in the shape of resistive elements (which are electrically isolated from the substrate 70), the layer 72 is thermally oxidized to form an oxide passivation layer 76 (FIG. 5). Contacts 78 are etched into the polysilicon resistors 74 (FIG. 6) followed by sputter deposition of an aluminum film 80 (e.g., 0.4 micrometers thick) (FIG. 7). Aluminum interconnects 82 (see FIG. 10) are sputtered and patterned to connect the polysilicon resistors 62 thus formed into a pressure/flow sensor circuit and to aluminum pads 84 (e.g., 1 mm×1 mm) (see FIG. 2), which serve as connectors for bonding wires to the tool 40. The remaining exposed silicon nitride layer 72 is patterned in a conventional front-back side alignment system to create the horn shape of the needle half parts 50, 52 and the grooves that will define the fluid flow channel 48 in the tool needle structure. For example, the exposed silicon may be etched in 5% TMAH solution with salicylic acid as an aluminum passivation additive. The TMAH etch ensures aluminum passivation and compatibility with integration of active electronic devices on the tool 40. Another etch opening on the back side of one 50 of the half needles results in a silicon nitride membrane 64 (e.g., a square membrane 1 $\mu$m×600 $\mu$m×600 $\mu$m), which forms the pressure sensing component in the pathway of the fluid flow channel 48. (FIG. 8.) The half needle body 50 with polysilicon resistors 62 and silicon nitride membrane 64 formed thereon in the manner just described is then bonded with the other corresponding half needle body part 52, e.g., using silk-screened adhesive, to form the body 42 of the tool 40 with a pressure/flow sensor integrally formed thereon (FIG. 9).

Figure 11:
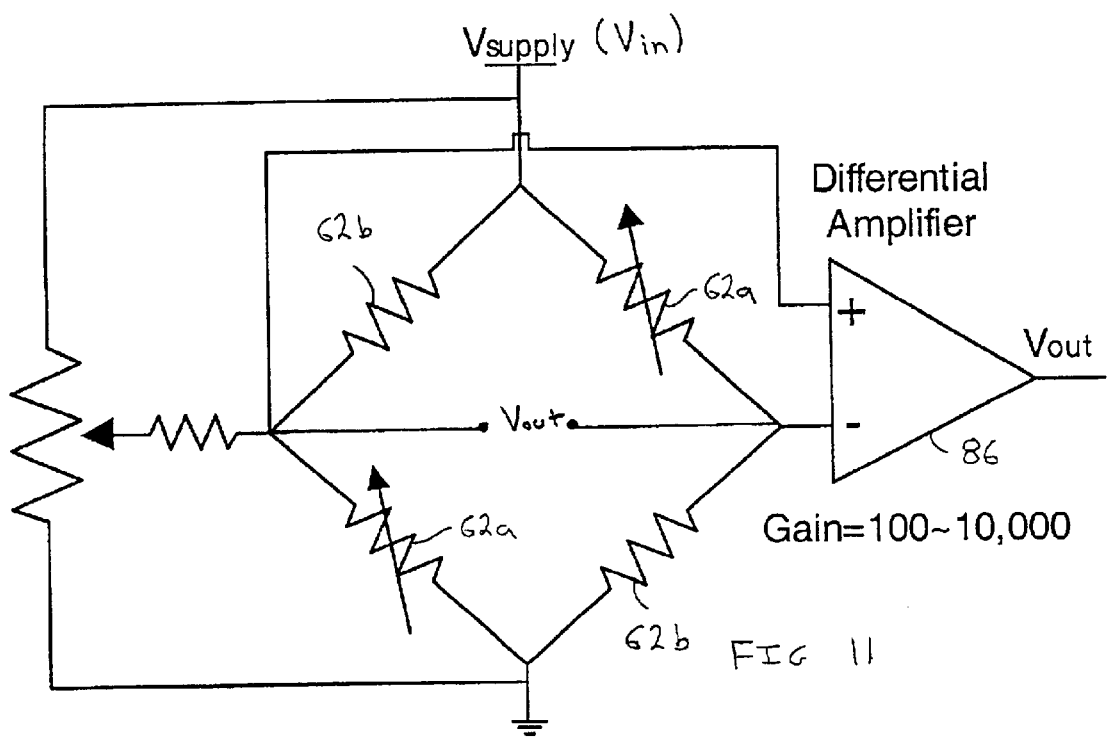
FIG. 11 is a schematic circuit diagram of a Wheatstone bridge circuit which may be formed by polysilicon resistors integrally formed on a silicon surgical tool in accordance with the present invention to form an integrated pressure/flow sensor, and following circuits.

The polysilicon resistors 62 forming the pressure/flow sensor 60 are preferably formed in positions on the tool body 42 with respect to the membrane 64, and connected together via the aluminum interconnects 82, to form a Wheatstone bridge circuit configuration. As shown in FIGS. 9–11, two resistors 62a are preferably formed at positions at the center of the edge of the membrane 64, where the maximum stress in the membrane is generated. Two other polysilicon resistors 62b are formed on the solid silicon substrate of the tool body 42, so that their resistance does not change with pressure flow changes in the fluid flow channel. The alignment of these resistors is chosen to be perpendicular to the longitudinal vibrating direction of the silicon horn forming the body 42 of the tool, so less high frequency ultrasonic signals caused by tool vibration will be coupled into the low frequency pressure signal derived from the Wheatstone bridge pressure/flow sensor circuit 60. Because transverse gage factor and longitudinal gage factor always have opposite signs for polysilicon resistors, the corner parts of the polyresistors do not contribute to and actually reduce the total change of resistance under stress. The polysilicon resistors may be positioned on the tool 40 such that the return path is located 31% of the membrane length away from the sides, where the stress in the membrane is zero. A two-stage instrumentation amplifier 86 (constructed from, e.g., Linear Technology, Inc. LT1113 op-amps) may be used to amplify the differential signal from the pressure sensor circuit, with adjustable amplification up to 10,000. A low pass filter circuit is preferably used to filter the signal at ultrasonic frequencies.

Figure 12:
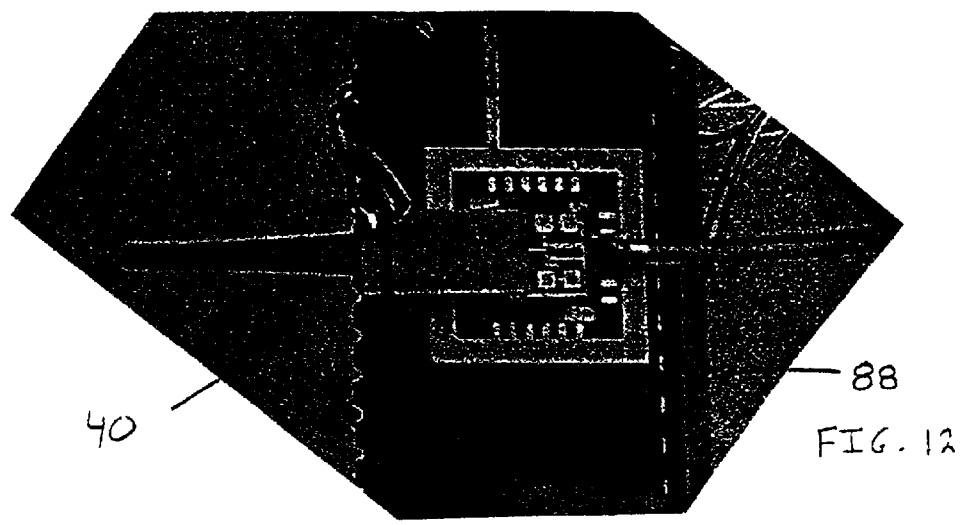
FIG. 12 is a detailed plan view of a micromachined silicon surgical tool with an integrated pressure/flow sensor formed thereon in accordance with the present invention as bonded to an integrated circuit DIP package.
Figure 13:
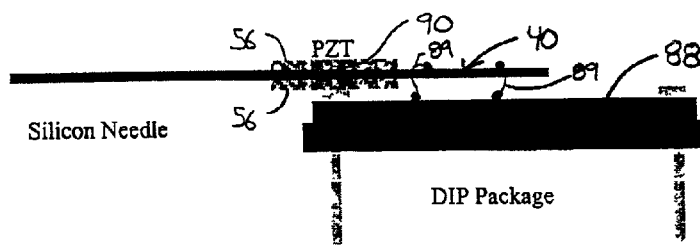
FIG. 13 is a schematic side view of the micromachined silicon surgical tool in accordance with the present invention as bonded to an integrated circuit DIP package as shown in FIG. 12.

The entire structure forming the micromachined silicon tool 40 may be bonded onto an integrated circuit DIP package 88 or some other mounting structure, as shown in FIGS. 12 and 13. The aluminum pads 84 formed on the tool 40 may then be wire-bonded 89 to the pins of the DIP package and, e.g., connected to a conventional supply and amplifier circuit formed thereon. Such a circuit provides, in a conventional manner, a desired supply voltage to the Wheatstone bridge pressure sensor circuit 60 formed on the tool 40, and receives, amplifies, and filters, in a conventional manner, an electrical signal from the sensor circuit 60 responsive to pressure in and/or flow through the fluid flow channel 48 of the tool 40.

Preferably, the micromachined silicon tool 40 is bonded to the packaging 88 at a null point or displacement node 90 of the horn/needle structure forming the body 42 of the tool 40, as shown in FIG. 13. The actuators 56 are preferably also bonded to the tool 40 at this displacement node point 90. This minimizes coupling of the ultrasonic vibration of the tool 40 to the packaging 82 and circuitry formed thereon.

Figure 14:
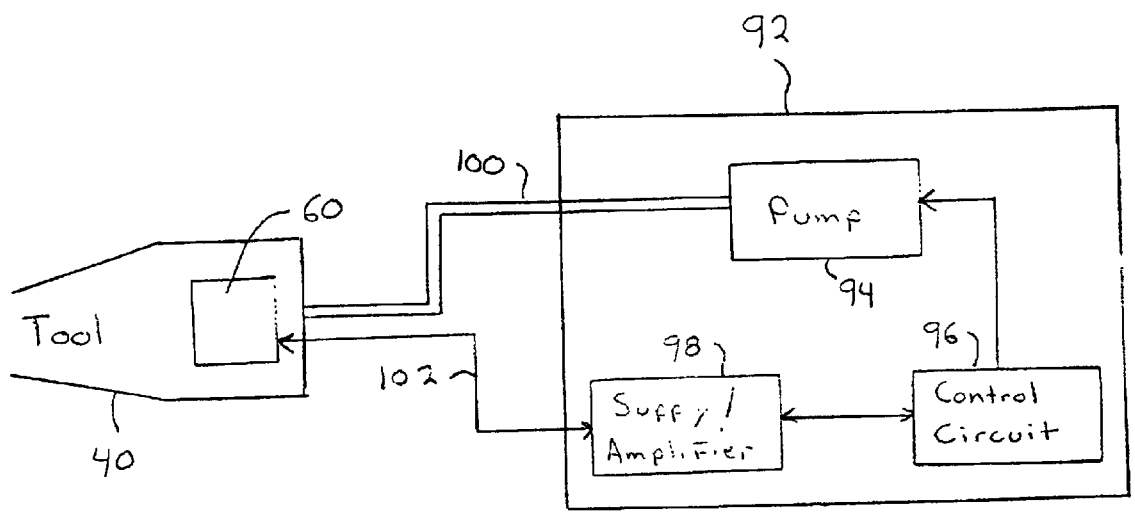
FIG. 14 is a schematic block diagram of an exemplary feedback control system for controlling the aspiration of fluid through a surgical tool with an integrated pressure/flow sensor thereon in accordance with the present invention.

As illustrated in the schematic diagram of FIG. 14, a pressure/flow sensor 60 integrally formed on a surgical tool 40 may be employed to provide an accurate and timely feedback signal for a pumping system used to pump fluid through the flow channel 48 formed in the tool 40. Such a pumping system may be remotely located from the tool 40, and may include a pump 94, e.g., a peristaltic pump, a control circuit 96, and a voltage supply/amplifier circuit 98. The pump 94 may be connected by a tube 100, e.g., conventional silicone tubing, to the fluid flow channel 48 of the tool 40, e.g., via the grommet 54 formed on the proximal end 46 of the tool 40 for this purpose. The supply/amplifier circuit 98 is connected by wiring 102 to the pressure/flow circuit 60 on the tool 40. As discussed above, the supply/amplifier circuit 98, or portions thereof, may be provided on the integrated circuit packaging upon which the tool 40 is mounted. The supply/amplifier circuit 98 provides a voltage supply to, e.g., the Wheatstone bridge sensor circuit formed on the tool 40. The supply/amplifier circuit 98 provides an amplified signal responsive to changes in conditions in the fluid channel 48 formed in the tool 40, as provided by the sensor circuit 60, to the control circuit 96. The control circuit 96 may be implemented in a conventional manner as an analog and/or digital circuit. The control circuit 96 controls operation of the pump 94 and, therefore, of the pressure in and fluid flow through the fluid flow channel 48 formed in the tool 40. Thus, feedback provided to the control circuit 96 by the pressure/flow sensor 60 via the supply/amplifier circuit 98 allows the control circuit 96 to control the pump 94 to smooth out pressure and flow transients within the fluid flow channel 48. Since the integral sensor 60 provides an electrical feedback signal which is rapidly and accurately responsive to pressure/flow changes in the fluid flow channel 48, the control circuit 96 can control the pump 94 to respond rapidly and accurately to such changes. For example, an occlusion of the fluid flow channel 48 during use of the tool for phacoemulsification will result in a sudden rise in pressure within the fluid flow channel 48. This rise will be detected rapidly and accurately by the integral sensor 60 on the tool 40, and provided as an electrical signal to the control circuit 96, via the supply/amplifier circuit 98. Thus, the control circuit 96 can respond rapidly to the sudden increase in pressure by turning off or otherwise controlling the pump 94 to reduce pressure until the occlusion is cleared.

Figure 15:
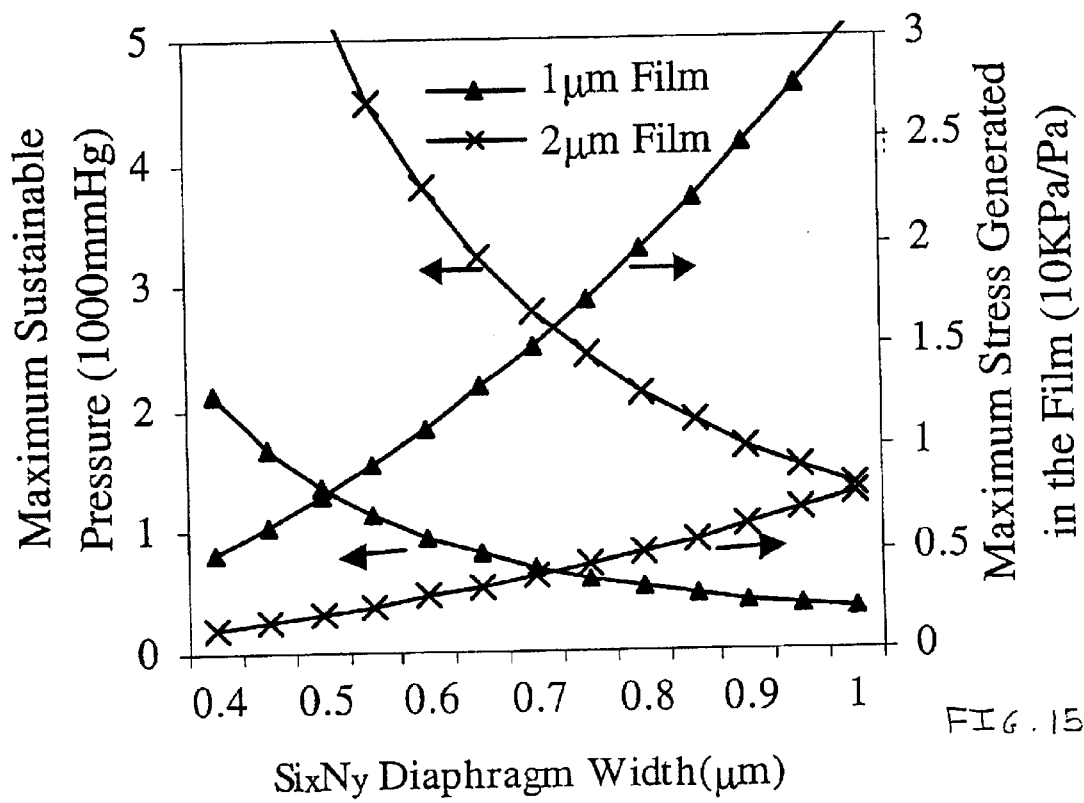
FIG. 15 is a graph showing the influence of membrane size on pressure sensitivity and maximum sustainable pressure of a pressure sensor integrally formed on a micromachined silicon surgical tool in accordance with the present invention.

In designing a pressure sensor to be integrally formed as part of a micromachined silicon surgical tool, it is important to insure that the membrane 64 portion of the sensor be able to sustain the stresses generated in the fluid flow channel 48 of the tool 40 during desired applications. For example, for phacoemulsification, a silicon-nitride membrane pressure sensor should be able to sustain large stresses generated during suction (400 mm Hg is the typical suction vacuum used in phacoemulsification surgery). However, it should be noted that there is a trade-off between membrane strength and higher sensitivity. For a given membrane thickness, the smaller the membrane size, the larger the maximum pressure it can sustain, but also the smaller generated stress, which results in lower sensitivity. FIG. 15 shows the influence of membrane (diaphragm) size on maximum applicable pressure and maximum membrane stress generated under one Pascal load pressure. The curves are calculated assuming linear plate theory (stress generated in the diaphragm is proportional to load pressure), which over estimates the maximum generated stress under large load pressure, but still provides a reliable evaluation on both the sensitivity and strength of the pressure sensing diaphragm. Membrane size should be chosen to give maximum sensitivity while still sustaining enough pressure load to assure enough safety margin for use in the contemplated application (e.g., 800 mm Hg for use in phacoemulsification surgery).

Figure 16:
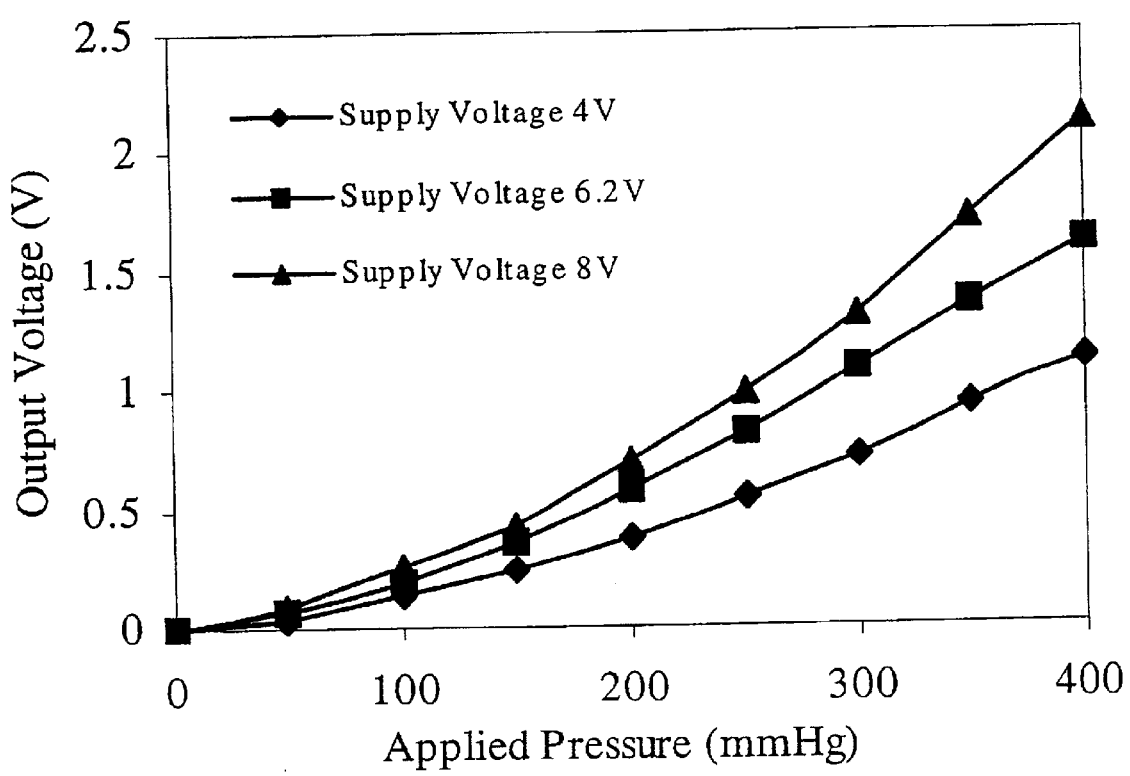
FIG. 16 is a graph showing exemplary static pressure measurements at various supply voltage levels for a pressure sensor integrally formed on a micromachined silicon surgical tool in accordance with the present invention.

FIG. 16 illustrates the static pressure response of an integrated pressure sensor 60 formed on a micromachined silicon surgical tool in accordance with the present invention. The experimental results illustrated were generated by feeding air or water into an occluded fluid flow channel 48 formed in a tool 40 in accordance with the present invention with a sphygmomanometer. The non-linear response of the membrane/polysilicon resistor sensor circuit 60 is believed to be due to a non-linear piezoresistivity of the polysilicon resistors.

Figure 17:
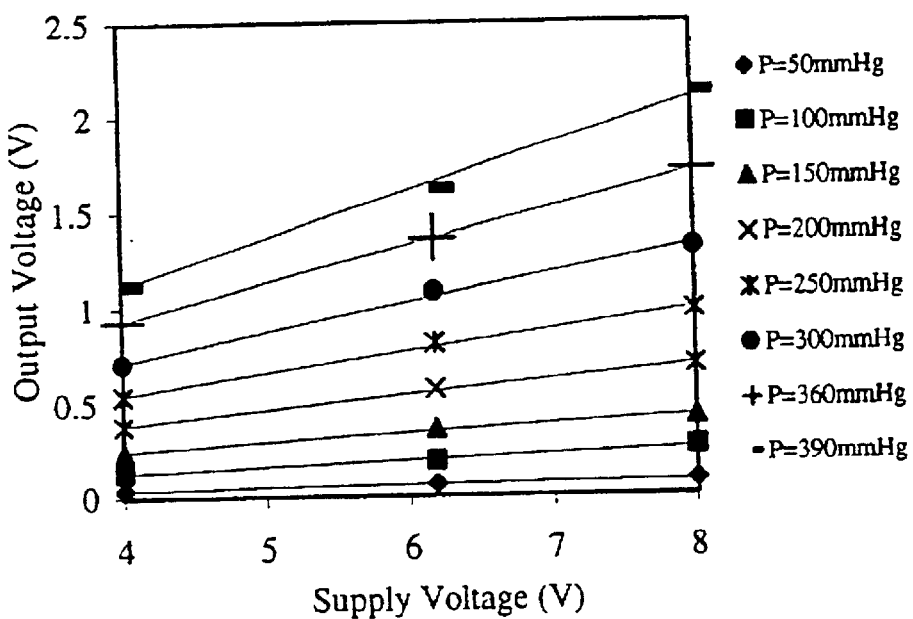
FIG. 17 is a graph showing the dependence of pressure sensor output on supply voltage of a pressure sensor integrally formed on a micromachined silicon surgical tool in accordance with the present invention.

FIG. 17 shows exemplary experimental output signals provided from an integrated pressure circuit 60 integrally formed on a micromachined silicon surgical tool 40 in accordance with the present invention, as a function of supply voltage at different pressure loads. The measurement was done for pressures up to 400 mm Hg and the dependence of output signal on supply voltage was found to be linear. This indicates that, in static pressure testing conditions, the signal is independent of thermal effects, which would have resulted in a quadratic relationship between output signal and supply voltage.

Figure 18:
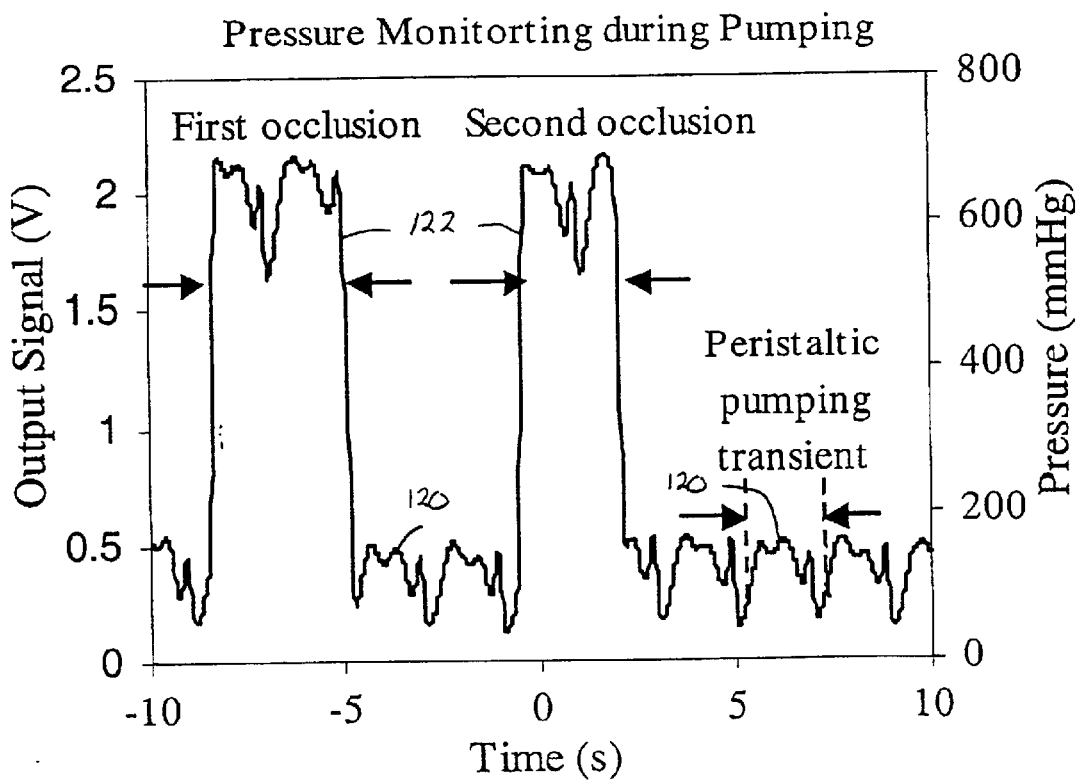
FIG. 18 is a graph illustrating the exemplary responsiveness to pressure changes in the fluid flow channel of a surgical tool of a pressure sensor mounted on the tool in accordance with the present invention.

Experimental results using a silicon microsurgical tool 40 in accordance with the present invention are illustrated in FIG. 18. The silicon microsurgical tool was driven at 150 kHz, 50 V peak-to-peak, to cut boiled egg white and swine eye lenses. The fluid flow channel 44 was coupled to a peristaltic pump to aspirate the fragments. The signal from the integrated pressure sensor provided instant and continuous information about the pressure condition in the fluid flow channel. FIG. 18 shows the pressure monitoring output signal while water is pumping through the fluid flow channel at 2.4 ml/s. The periodic pressure transients 120, due to peristaltic pump action, were approximately 120 mm Hg. Two occlusions during this time period were observed, and the pressure increase in the channel due to occlusions at the distal end of the channel were measured to be approximately 600 mm Hg. From this experiment, without feedback, it is shown that large amounts of excessive pressure builds up and breaks down suddenly during occlusion cycles, which necessitates a fast-responding monitoring and control system. A surgical tool with an integrated pressure sensor 60 in accordance with the present invention makes such a system possible.

Figure 19:
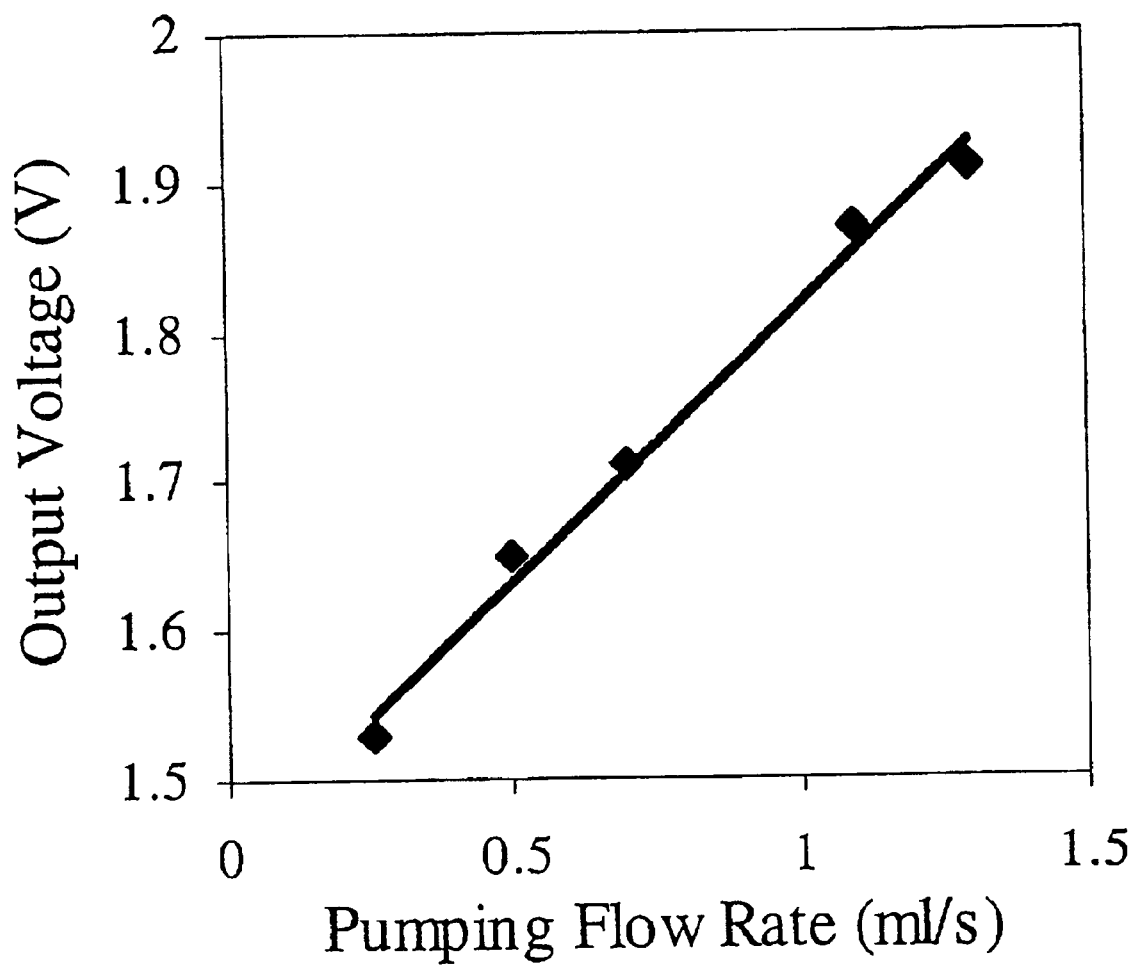
FIG. 19 is a graph showing the response of a flow sensor mounted on a surgical tool in accordance with the present invention to changing flow rates through a fluid flow channel formed in the tool.

The exemplary sensor 60 described herein for sensing pressure in the fluid flow channel 48 of a surgical tool 40 may also be used to sense fluid flow through the fluid flow channel 48. The sensor 60 is able to sense flow due to flow-induced heat loss of the Joule-heating of the sensor resistors 62. Fluid flow in the fluid flow channel 48 modifies the heat transfer from the piezoresistors 62 formed on the membrane 64. The resistance change due to flow can be sensed by measuring the total resistance change in one arm of the Wheatstone bridge, while the resistance change due to pressure is sensed by the differential signal from two arms of the bridge. FIG. 19 shows the results of flow measurement at 8V supply voltage. The flow sensitivity is measured to be 0.36 V/(ml/s).

Under free flow (non-occluded) conditions, the output signal provided by the sensor 60 can result from both flow and pressure effects. Thus, both flow (F) and pressure (P) signals can be obtained, according to a simple model, by applying two different supply voltages in sequence and the following equations:

$$V_{out1} = \alpha P V_{in1} + \beta V_{in1}^2 F$$

and $$V_{out2} = \alpha P V_{in2} + \beta V_{in2}^2 F,$$

where $\alpha$ and $\beta$ are piezoresistive and heat transfer effect constants, respectfully. The two equations may then be solved for the two unknowns P and F. Note that the flow signal F is proportional to the square of the input voltage whereas the signal P related to pressure is linearly proportional to the input voltage.

It should be understood that the present invention is not confined to the particular exemplary embodiments and applications thereof described herein for illustration, but embraces all forms thereof as come within the scope of the following claims.

What is claimed is:

1. A surgical tool, comprising:
   (a) a rigid body including a needle shaped portion for passing into tissue and defining a flow channel extending therethrough for passing a flow of fluid through the tool; and
   (b) a sensor responsive to a condition in the flow channel and integrally attached to the rigid body wherein the sensor includes a membrane on the rigid body in fluid communication with the flow channel and having a membrane thickness which is less than a thickness of the rigid body wherein the sensor includes at least one resistor formed on the membrane, and wherein the sensor includes at least one resistor formed on the rigid body near the membrane.

2. The surgical tool of claim 1 wherein the resistors formed on the membrane and on the rigid body are connected together in a circuit configuration.

3. The surgical tool of claim 2 wherein the sensor includes two resistors formed on the membrane and two resistors formed on the rigid body near the membrane, wherein the resistors formed on the membrane and the rigid body are connected together in a Wheatstone bridge circuit configuration.

4. A micromachined silicon tool, comprising:
   (a) a tool body formed of micromachined silicon and defining a flow channel extending therethrough for passing a flow of fluid through the tool; and
   (b) a sensor responsive to a condition in the flow channel and integrally attached to the tool body, wherein the sensor includes a membrane formed on the tool body in fluid communication with the flow channel and having a membrane thickness which is less than a thickness of the tool body, wherein the sensor includes at least one resistor formed on the membrane, and wherein the sensor includes at least one resistor formed on the tool body near the membrane.

5. The micromachined silicon tool of claim 4 wherein the resistors formed on the membrane and on the tool body are connected together in a circuit configuration.

6. The micromachined silicon tool of claim 5 wherein the sensor includes two resistors formed on the membrane and two resistors formed on the tool body near the membrane, wherein the resistors formed on the membrane and the rigid body are connected together in a Wheatstone bridge circuit configuration.

7. A micromachined tool, comprising:
   (a) a tool body having a flow channel extending therethrough for passing a flow of fluid through the tool;
   (b) a membrane on the tool body in fluid communication with the flow channel and having a membrane thickness which is less than a thickness of the tool body; and
   (c) at least one resistor formed on the membrane; and
   (d) at least one resistor formed on the tool body near the membrane.

8. The micromachined tool of claim 7 wherein the tool body is micromachined from silicon.

9. The micromachined tool of claim 8 wherein the membrane is made of silicon nitride.

10. The micromachined tool of claim 8 wherein the at least one resistor formed on the membrane is a polysilicon piezoresistor.

11. The micromachined tool of claim 7 wherein the resistors formed on the membrane and on the tool body are connected together in a circuit configuration.

12. The micromachined tool of claim 11 wherein two resistors are formed on the membrane and two resistors are formed on the tool body near the membrane and wherein the resistors formed on the membrane and the tool body are connected together in a Wheatstone bridge circuit configuration.

* * * * *